United States Patent
Lin et al.

(10) Patent No.: US 7,820,794 B2
(45) Date of Patent: Oct. 26, 2010

(54) LONG-LASTING COLLAGEN AND MANUFACTURING METHOD THEREOF

(75) Inventors: Feng-huei Lin, Sinshih Township, Tainan County (TW); Bo-chung Chan, Sinshih Township, Tainan County (TW); Hsiang-yin Lu, Sinshih Township, Tainan County (TW); Yu-te Lin, Sinshih Township, Tainan County (TW)

(73) Assignee: Sunmax Biotechnology Co., Ltd., Tainan (TW)

( * ) Notice: Subject to any disclaimer, the term of this patent is extended or adjusted under 35 U.S.C. 154(b) by 34 days.

(21) Appl. No.: 12/208,616

(22) Filed: Sep. 11, 2008

(65) Prior Publication Data

US 2010/0063253 A1  Mar. 11, 2010

(51) Int. Cl.
*A61K 38/17* (2006.01)
(52) U.S. Cl. .................................................. 530/356
(58) Field of Classification Search ................. 530/356
See application file for complete search history.

*Primary Examiner*—Suzanne M. Noakes
(74) *Attorney, Agent, or Firm*—Chun-Ming Shih

(57) ABSTRACT

In a long-lasting collagen and its manufacturing method, a pig skin is gone through processes of scraping extra tissues, removing fats, imbibition, digesting, centrifugal separation, salting-out, collecting lower-layer precipitate and freeze-drying to form a collagen, and the collagen is mixed with γ-PGA, and then a glutaraldehyde solution is added and mixed uniformly to perform a first crosslinking and form the long-lasting collagen, so as to overcome the shortcomings of a conventional collagen having a short storage time, a requirement of applying the collagen repeatedly, and a high concentration of remained glutaraldehyde which is biologically poisonous to human bodies.

17 Claims, 4 Drawing Sheets

LONG-LASTING COLLAGEN AND MANUFACTURING METHOD THEREOF

BACKGROUND OF THE INVENTION

1. Field of Invention

The present invention relates to a long-lasting collagen and its manufacturing method, and more particularly to a method of producing a collagen by adding γ-polyglutarmic acid (γ-PGA) to the collagen and going through two crosslinking processes to obtain the long-lasting collagen. The invention not only increases the storage time of the collagen in human body, but also achieves a better biocompatibility and provides a higher value for practical applications.

2. Description of Related Art

As we get older, our skin ages and loses its charm and healthy glow, causing wrinkles and tough inelastic skins, since the metabolic capability of dermis under the skin reduces with age, and the dermis is a main factor of the elasticity of skin. Reduction in the metabolic capability of skin will lead to skin aging, and thus various different rejuvenation methods are developed and available in the market. Among these rejuvenation methods, facial filler gives the best effect so far, and facial filler can be divided into two main types of materials: a synthetic material and a natural material. The synthetic material includes: silicone, hydroxyapatite (HAP), polylactic acid (PLA), polymethyl methacrylate (PMMA) and hydroxyethylmethacrylate (HEMA), etc. The natural material includes: botox (BT), autologous fat, collagen and hyaluronic acid (HA), etc.

However, the synthetic facial filler has the following drawbacks:

1. Silicone exists permanently in human body after being injected into the human body and it will cause long term inflammation and granulomas, and thus the silicone must be removed by operation. In addition, silicon may migrate due to gravitational force, and thus U.S. Food and Drug Administration (FDA) prohibits applying silicon into human beings by laws.

2. In a hydroxyapatite (HAP) material such as Radiesse, the only facial filler meeting the laws and regulations set forth by the U.S. Food and Drug Administration (FDA). Although HAP can be maintained for 2 to 5 years, nodule may occur sometime, particularly at the positions of mouth and lip, and it gives a bad look.

3. Poly 1-lactic acid (PLLA) is generally used as an injection material. Although PLLA has been approved by U.S. Food and Drug Administration (FDA), granulomas may still occur, and PLLA has the highest frequency of occurrence of granulomas among all facial fillers.

4. Polymethyl methacrylate (PMMA) comes with an excellent biocompatibility, but it cannot be degraded in human body and becomes a bio-accumulative substance. Although PMMA is a permanent implantation material, granulomas also occurs easily, and thus many countries have banned the use of polymethyl methacrylate (PMMA) for hypodermic injection.

5. Hydroxyethylmethacrylate (HEMA) has a drawback similar to that of the polymethyl methacrylate (PMMA), but it contains a hydroxyl radical (—OH), and thus its elasticity is enhanced after being applied. However, PMMA will be hardened as time goes by.

In summation, the shortcomings of the synthetic facial filler material reside on its causing serious inflammations and having major side effects on human bodies.

Further, the natural facial fillers also have the following drawbacks:

1. Botox (BT) disables some of the biological functions of nerves and muscles by holding back the release of acetylcholine to achieve the effect of removing dynamic wrinkles, but botox (BT) also disables some of the biological functions of muscles, and the muscles will be degenerated after a period of time, and the facial expression of a patient will be unnatural when smiling. As the muscle activity is reduced, patients have to massage the injecting position everyday. In addition, researches reports show that there is 1% of fatal risk for an overdose of botox (BT).

2. Autologous fat is made of a material coming from a patient's autologous fat, and thus the biocompatibility is very high, but the time for the autologous fat to be remained in human varies greatly due to the fat source and the individual difference of the patient, and the time varies from months to years. On the other hand, the autologous fat has larger particles that cannot fill wrinkles or small lines in a small area, and thus the effect and range are very limited.

3. There are different collagens including human collagens, cadaveric collagens, bovine collagens and porcine collagens, etc, wherein the bovine collagen has been used for more than 20 years, and approved by the U.S. Food and Drug Administration (FDA). As mad cow disease existed in both animals and humans explodes and has the risk of infection. Although human collagen has passed the approval of the U.S. Food and Drug Administration (FDA), human collagen is not available easily, and its price is higher than other materials. The cadaveric collagen is also not available easily as the human collagen, and the particle size is larger than the human collagen falling within a range of micrometer (μm) and millimeter (mm) due to the factor of cultivation environment, and thus a thicker and larger needle is needed and it will cause additional pain to patients.

4. Since hyaluronic acid (HA) is a polysaccharide composed of two monomers (such as N-acetyglucosamine and D-glucuronic acid) that can go through a complete metabolism, but the structure of the monomer (such as N-acetyglucosamine) is very close to heparin, such that if there is a wound, the monomer (N-acetyglucosamine) will be used for filling, and the quantity of hyaluronic acid (HA) will be reduced. Since hyaluronic acid (HA) can enhance the combination of matter under the dermis and cannot make the skin elastic, therefore it is necessary to avoid the wound from being pressed by external forces and further hurting the wound after the implantation. On the other hand, the movement of muscles accelerates the absorption of hyaluronic acid (HA), and thus patients have to avoid excessive facial expressions.

In summation of the foregoing materials of the natural and synthetic facial fillers, the level of inflammation caused by collagens is the lowest, and thus collagens can be used extensively, but they still have the following drawbacks:

1. The time of collagens remained in human body is short, and uncrosslinked collagens will be degraded and absorbed in human body within three months, and collagens crosslinked by a crosslinking agent such as glutaraldehyde can remain a human body for six months, which is still too short, so that patients have to apply an injection for the supplement frequently, and it causes tremendous inconvenience.

2. Collagens are biological poisonous, and the collagens crosslinked by glutaraldehyde have a high concentration of remained glutaraldehyde, which is biologically poisonous and harzardous to human health.

Obviously, the conventional collagens still have many drawbacks and require further improvements.

SUMMARY OF THE INVENTION

In view of the foregoing shortcomings of the conventional collagen with short storage time and biological poison, the inventor of the present invention based on years of experience in the related industry to conduct extensive researches and experiments, and finally developed a long-lasting collagen and invented a manufacturing method of the collagen in accordance with the present invention to overcome the shortcomings of the prior art.

Therefore, it is a primary objective of the present invention to provide a long-lasting collagen, wherein a γ-polyglutarmic acid (γ-PGA) is added into a collagen and gone through a crosslinking process twice to obtain a long-lasting collagen with a uniformly and completely crosslink and a storage time increased by two to three times, so as to overcome the shortcomings of the conventional collagens having a short storage time and requiring an injection for suppment frequently.

Another objective of the present invention is to provide a low biologically poisonous collagen that uses glutaraldehyde of a very low concentration to uniformly and completely cross link the collagen with the glutaraldehyde to obtain remained glutaraldehyde of a very low concentration while providing a collagen with a better biocompatibility, so as to overcome the shortcomings of the conventional collagen having a high concentration of remained glutaraldehyde and a biologically poisonous glutaraldehyde that are harmful to our health.

BRIEF DESCRIPTION OF THE DRAWINGS

The invention, as well as its many advantages, may be further understood by the following detailed description and drawings in which.

DETAILED DESCRIPTION OF THE INVENTION

To make it easier for our examiner to understand the technical measures and operating procedure of the invention, we use preferred embodiments together with the attached drawing for the detailed description of the invention.

Figure 2:
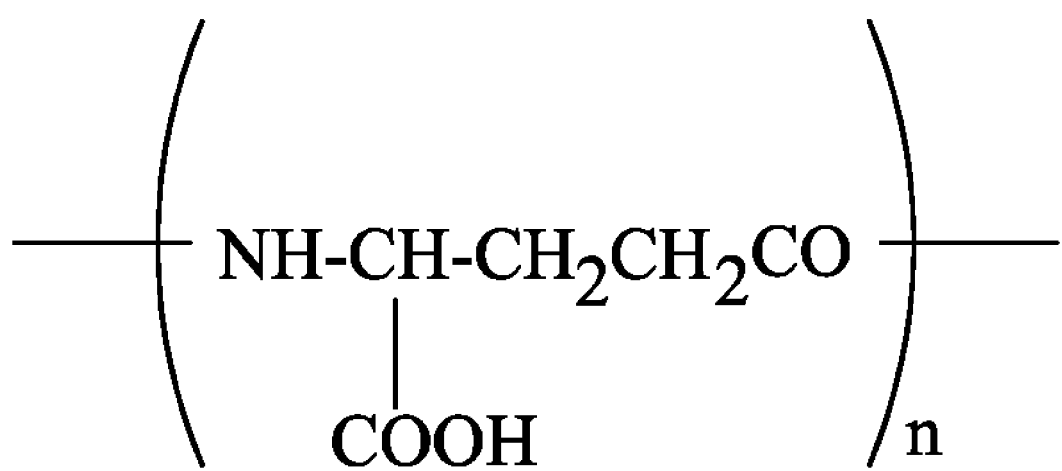
FIG. 2 is a schematic view of the chemical structure of γ-polyglutarmic acid (γ-PGA)

The present invention discloses a long-lasting collagen and its manufacturing method, wherein a collagen is prepared, and a γ-polyglutarmic acid (γ-PGA) is added into the collagen, while going through a predetermined manufacturing process to obtain a long-lasting collagen. The chemical structure of γ-polyglutarmic acid (γ-PGA) is shown in FIG. 2, and the amine linkage (—CONH) formed by linking an amino group (—NH$_2$) of the γ-polyglutarmic acid (γ-PGA) and a carbonyl group (—COOH) of a (residue group) which is called γ-linkage, and the linkage is relatively not easy to be degraded rapidly by the attack of an enzyme in human body, and the γ-polyglutarmic acid (γ-PGA) significantly resists the degrade of enemzes in human body to greatly retard the degrade of collagens in human body.

Figure 1:
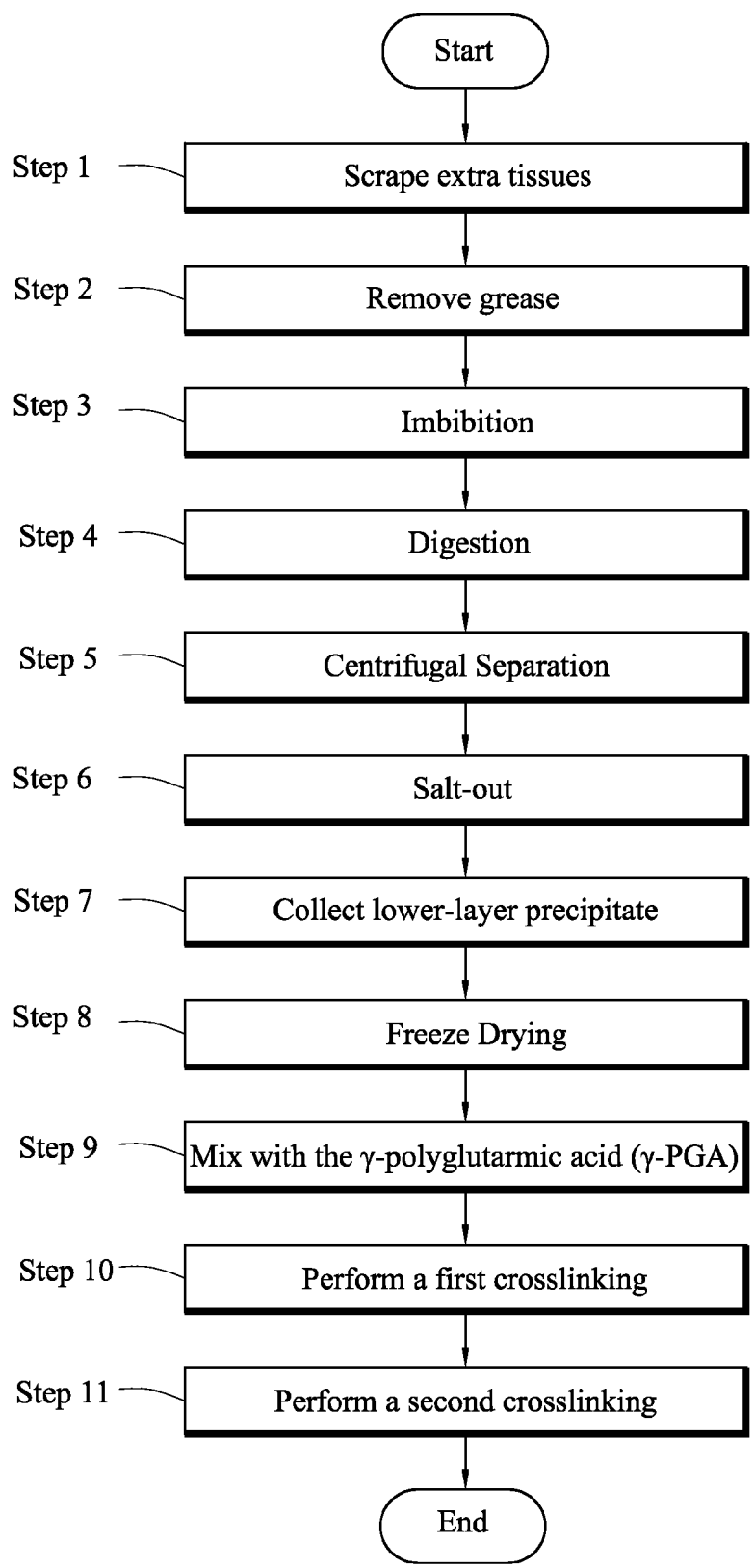
FIG. 1 is a flow chart of the present invention.

With reference to FIG. 1, the long-lasting collagen is manufactured by the following procedure:

Step 1: Scrape extra tissues: Firstly, scrape extra muscle and fat tissues, and cut the remaining portion into small segment tissues.

Step 2: Remove grease: Dip the small segment tissues in acetone to remove grease, and rinse the small segment tissues twice until the grease is removed completely.

Step 3: Imbibition: Dip the degreased small segment tissues in salt water (with a concentration is 1%) at a predetermined temperature (4° C.) for a predetermined time (24 hours), and then dip it in citric acid solution of a specific pH value (4.5) for the predetermined time for the imbibition of the small segment tissues.

Step 4: Digestion: Dip the imbibited small segment tissues in a first solution (which is a mixed solution of pepsin and hydrochloric acid with a concentration of 0.5M) at the predetermined temperature for the predetermined time to digest the small segment tissues into a second solution.

Step 5: Centrifugal Separation: Separate the digested small segment tissues from the second solution by performing a centrifugal separation of the second solution in a first predetermined condition (wherein the weight of the second solution is equal to 5500 g).

Step 6: Salt-out: Add a salt water solution into the second solution to prepare a third solution (with a concentration of 0.8M), while shaking the solution severely until a cloudy substance if formed.

Step 7: Collect lower-layer precipitate: Perform the centrifugal separation to the third solution in a second predetermined condition (wherein the weight of the second solution is equal to 22000 g) while collecting a lower-layer precipitate, and then place the lower-layer precipitate in water twice, while adding sodium hydroxide (NaOH) with a concentration of 0.1N) to adjust the pH value to form a fourth solution (with a pH value of 7).

Step 8: Freeze Drying: Freeze the fourth solution at another predetermined temperature (−20° C.) for the predetermined time, and then dry the solution to obtain a collagen (which is a Type I collagen).

Step 9: Mix with the γ-polyglutarmic acid (γ-PGA): Prepare the collagen as a collagen solution (with a concentration of 35 mg/ml), while mixing a predetermined quantity (4 ml) of the collagen solution with the same predetermined quantity of γ-polyglutarmic acid (γ-PGA) to produce a fifth solution.

Step 10: Perform a first crosslinking: Titrate another predetermined quantity (0.5 ml) of glutaraldehyde solution (with a concentration of 0.05%) in the fifth solution by a pump (which is a tubing pump) while blending the solution at a predetermined rotating speed (250 rpm) for another predetermined time (30 minutes) to perform a first crosslinking to the collagen and glutaraldehyde in the fifth solution.

Step 11: Perform a second crosslinking: Finally, repeat Step 10 to complete the second crosslinking to obtain the long-lasting collagen.

The degrade-resisting effect of the long-lasting collagen of the invention can be proved according to a Bicinchoninic acid (BCA) testing procedure:

1. Uniformly mix a testing agent A and a testing agent B in a ratio of 50:1 by volume to prepare a BCA testing agent.

2. Add a sample A, a sample B and a sample C of 25 μl each into each groove of a 96-hole titration plate.

3. Add 200 μl of the BCA into each groove, and let it sit still at 37° C. for 30 minutes, such that each sample is reacted completely.

4. Finally, measure the absorption value of each group sample by an immune enzyme spectrophotometer, wherein the measuring wavelength is 650 nm.

In the preparation of the testing agent A, 40 mg of sodium tartrate ($Na_2C_4H_4O_6 \cdot 2H_2O$) is dissolved in 10 ml of 0.5M sodium hydroxide (NaOH) solution. After the sodium tartrate is dissolved completely, 1 g of sodium carbonate ($Na_2CO_3$) is added and blended with the solution until the solution is in a clear transparent state.

In the preparation of the testing agent B, 0.2 g of sodium tartrate ($Na_2C_4H_4O_6 \cdot 2H_2O$) is dissolved in 2 ml of 0.5M sodium hydroxide (NaOH). After the sodium tartrate is dissolved completely, deionized (DI) water is added until the volume of the solution reaches 10 ml, and finally 0.3 g copper sulfate ($CuSO_4$) is added into the solution until the solution is in a clear blue state.

The Group A sample is 4 ml of collagen solution at a concentration of 35 mg/ml.

The Group b sample is 4 ml of collagen solution at a concentration of 35 mg/ml, and 0.5 ml of the glutaraldehyde solution is dropped within one minute by the pump, while blending and mixing the solution uniformly at a rotating speed of 250 rpm to perform a first crosslinking. After the first crosslinking, 0.5 ml of glutaraldehyde solution is dropped, and blended to mix with the solution at a rotating speed of 250 rpm for 30 minutes to perform a second crosslinking. In the preparation of the glutaraldehyde solution, 400 μL of glutaraldehyde is dissolved into 7.6 ml of the phosphate-buffered saline (PBS) solution to complete preparing the glutaraldehyde solution at a concentration of 0.5%.

The Group C sample is the long-lasting collagen obtained from the manufacturing method in accordance with the present invention, and the BCA testing method is adopted for the testing, and thus it is necessary to dissolve the γ-polyglutarmic acid (γ-PGA) into a phosphate-buffered saline (PBS) solution for completing the testing.

Figure 3:
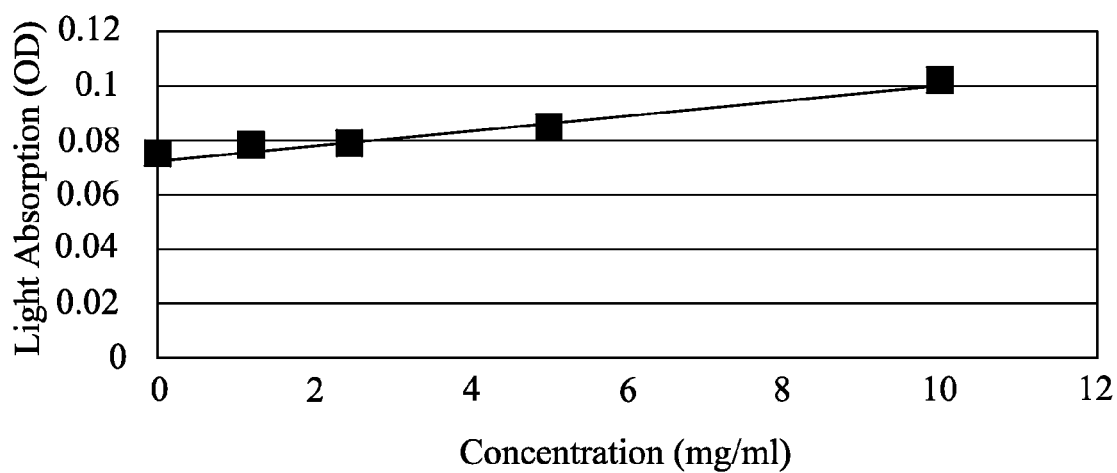
FIG. 3 is a curve of standard solutions of the collagen.

In addition, the BCA testing method is used for testing a standard collagen solution to obtain an absorption value x at a wavelength 650 nm of the standard collagen solution, while the absorption value x is substituted in an equation $y=0.002x+0.074$ to obtain a value of y, wherein the value of y in the equation indicates the concentration of peptide linkage in the standard collagen solution to obtain the graph of the standard collagen solution as shown in FIG. 3. In the figure, the relation of an absorption value at a wavelength 650 nm of the standard collagen solution versus a concentration of a peptide linkage is shown.

In the standard collagen solution, 2 ml of collagen at a concentration of 35 mg/ml is dissolved in 5 ml of 0.025N acetic acid solution, and then the phosphate-buffered saline (PBS) solution is diluted to complete the preparation of the standard collagen solution.

Figure 4:
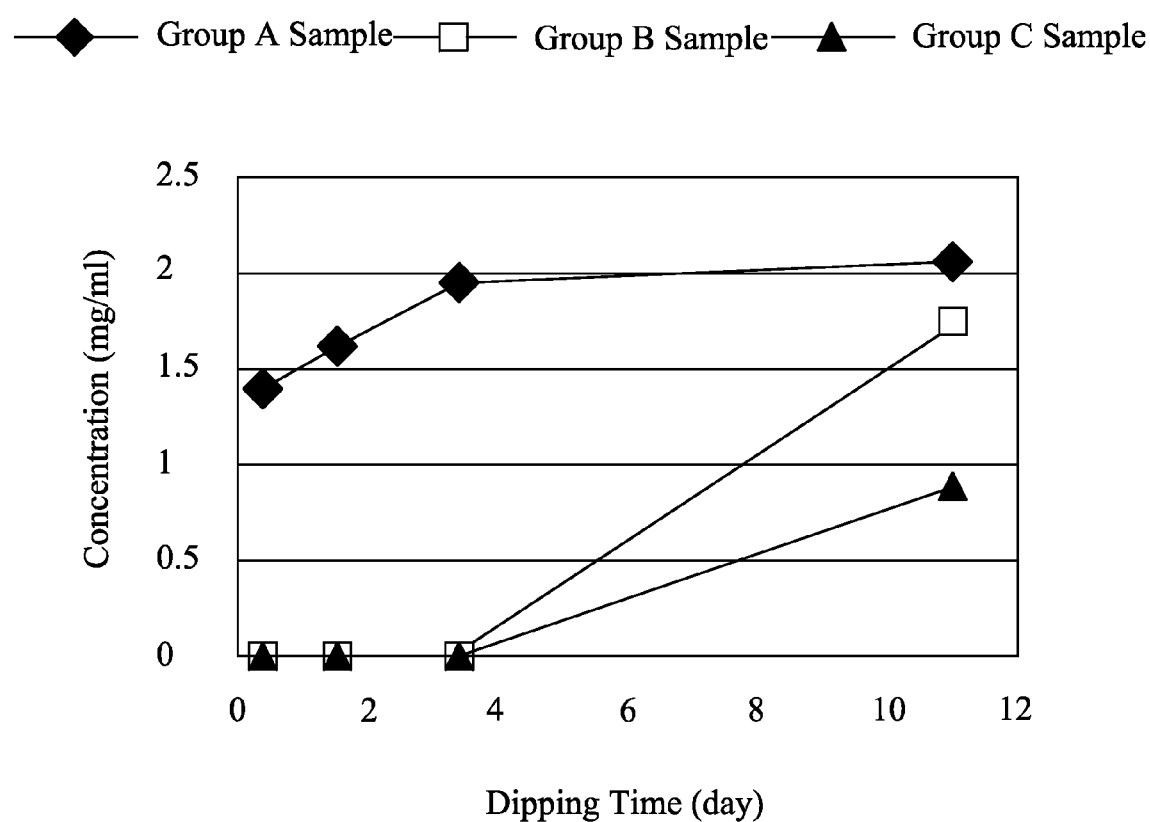
FIG. 4 is a schematic view of test results of Group A, B and C samples with the same concentration in the degrading speed of a collagenase.

With reference to FIG. 4 for Group A, B and C samples in collagenases of the same concentration, the testing results obtained by the BCA testing method show that: On the 11$^{th}$ day of the experiment, the concentration of the solution of Group A sample in the peptide linkage is 2.052 mg/ml; the concentration the solution of Group B sample in the peptide linkage is 1.77 mg/ml; and the concentration of the solution of Group C sample in the peptide linkage is 0.87 mg/ml. From the aforementioned results obtained from the same experimental conditions, the degrading speed of the Group C sample is much slower than the degrading speeds of the Group A and B samples, indicating that the Group C sample has a better resistance to the degrading effect and a slower degrading speed of the enzymes in human body approximately equal to half of that of the Group B sample. From the present clinical testing result, the Group B sample can be stored and remained in human body for 6~9 months, and thus we infer that the storage time of the Group C sample in human body is approximately equal to 12~18 months.

On the other hand, the γ-polyglutarmic acid (γ-PGA) in the the Group C sample is linked by a γ-linkage, and the amine linkage in human body is an α-linkage, and thus the enzyme for degrading the γ-linkage of a DNA sequence in a human body is in an inactivated state. Researches point out that it takes 6~7 months to activate this enzyme, and thus if a polypeptide of the γ-linkage enters into a human body, it will take at least 6~7 months to start degrading the polypeptide, indicating that a γ-polyglutarmic acid (γ-PGA) and a collagen polymer material (such as the Group C sample) takes at least 18~25 months to be degraded completely in human body.

A cell (a 3T3 fibroblast) is used for evaluating the biocompatibility of the Group A, B and C samples: the Group A, B and C samples are cultivated together with the cell for 3 days. With the following data, we can know about the information of cell activity, survival rate, quantity, senescence and genetic toxicity:

1. Mitochondrial activity assay (MTT): From the testing of the mitochondrial activity of the cells cultivated together with the Group A, B and C samples, we can know about the activity of the cells.

2. Lactate Dehydrogenase (LDH): From the testing of the Lactate Dehydrogenase (LDH) in the cells cultivated together with the Group A, B and C samples, we can measure the survival rate of the cells.

3. Total DNA Content: From the testing of the total DNA content in the cells cultivated together with the Group A, B and C samples, we can analyze the quantity of the cells.

4. b-galactosidase: From the testing of the b-galactosidase in the cells cultivated together with the Group A, B and C samples, we can measure the senescence of the cells.

5. Chromosome Aberration: A Giemsa stain is used to test the chromosome aberration cultivated together with the Group A, B and C samples, we can know about the genetic toxicity of the Group A, B and C samples to the cells.

The testing results are listed in the following table, wherein the control group in the table is the aforementioned standard collagen solution:

|  | Control Group | Group A Sample | Group B Sample | Group C Sample |
| --- | --- | --- | --- | --- |
| Mitochondrial activity assay (MTT) | 0.643 ± 0.154 | 0.682 ± 0.124 | 0.611 ± 0.173 | 0.692 ± 0.189 |
| Lactate Dehydrogenase (LDH) | 0.487 ± 0.094 | 0.503 ± 0.163 | 0.476 ± 0.120 | 0.511 ± 0.143 |
| Total DNA Content | 0.833 ± 0.144 | 0.789 ± 0.159 | 0.810 ± 0.201 | 0.805 ± 0.176 |
| b-galactosidase | 0.418 ± 0.067 | 0.512 ± 0.169 | 0.543 ± 0.112 | 0.498 ± 0.128 |
| Chromosome Aberration | 6.8% | 5.88% | 7.92% | 6.73% |

From the table above, we can observe that the Group A, B and C samples, the mitochondrial enzyme activity (MTT), lactate dehydrogenase (LDH), total DNA content, b-galactosidase and chromosome aberration are statistically consistent, and thus it shows that Group A, B and C samples do not contain cell poison and cause a change of chromosomes, and these samples have a good biocompatibility.

From the data as shown in the table, the main difference between the long-lasting collagen of the invention and the conventional collagen resides on that:

1. The invention complies with the novelty and improvement requirements of a patent application. In the present invention, the γ-polyglutarmic acid (γ-PGA) is added into a collagen and gone through a crosslinking process twice to obtain the long-lasting collagen, so as to overcome the shortcomings of the conventional collagen having a short storage time and requiring a frequent resupply of collagen by injection.

2. The invention complies with the practicability requirement of a patent application. In the present invention, glutaraldehyde of a low concentration goes through a crosslinking process twice to uniformly and completely crosslink the collagen with the glutaraldehyde to obtain a very low-concentration remained glutaraldehyde, while the long-lasting collagen has a better biocompatibility.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A manufacturing method of a long-lasting collagen, comprising the steps of:
   a) scraping extra muscle and fat tissues from a pig skin, and cutting the remaining portion of the pig skin into small tissue segment;
   b) dipping the small tissue segment into an organic solvent, and rinsing the small segment tissues until grease is removed completely;
   c) dipping the degreased small tissue segment in a salt water at a first predetermined temperature for a first predetermined time, and then in an acidic solution with a specific pH value for the first predetermined time to inhibit the small segment tissues;
   d) dipping the inhibited small tissue segment in a first solution at the first predetermined temperature for the first predetermined time to digest the small tissue segment into a second solution;
   e) perform a centrifugal separation of the second solution at a first predetermined condition to separate the digested small tissue segment from the second solution;
   f) adding a salt water solution into the separated second solution to prepare a third solution, while shaking the solution severely until a cloudy substance is formed;
   g) performing a centrifugal separation to the shaken third solution in a second predetermined condition while collecting a lower-layer precipitate, and putting the lower-layer precipitate into water while adding sodium hydroxide to adjust a pH value to form a fourth solution;
   h) freezing the fourth solution at a second predetermined temperature for the first predetermined time, and then drying the fourth solution to obtain a collagen;
   i) preparing the collagen into a collagen solution, and mixing the collagen solution with γ-polyglutamic acid (γ-PGA), both having a first predetermind quantity, into a fifth solution;
   j) titrating a second predetermined quantity of glutaraldehyde solution in the fifth solution by a pump, while blending the collagen of the fifth solution and the glutaraldehyde solution at a predetermined rotating speed for a second predetermined time to perform a first crosslinking; and
   k) titrating the second predetermined quantity of the glutaraldehyde solution in the fifth solution by the pump again, while blending at the predetermined rotating speed for the second predetermined time to perform a second crosslinking to obtain the long-lasting collagen.

2. The manufacturing method of a long-lasting collagen as recited in claim 1, wherein the organic solvent is acetone.

3. The manufacturing method of a long-lasting collagen as recited in claim 1, wherein the first predetermined temperature is 4° C.

4. The manufacturing method of a long-lasting collagen as recited in claim 1, wherein the acidic solution is a citric acid solution.

5. The manufacturing method of a long-lasting collagen as recited in claim 1, wherein the first solution is a mixed solution of pepsin and hydrochloric acid, having a concentration of 0.5M.

6. The manufacturing method of a long-lasting collagen as recited in claim 1, wherein the second predetermined temperature is −20° C.

7. The manufacturing method of a long-lasting collagen as recited in claim 1, wherein the collagen is a Type 1 collagen.

8. A manufacturing method of a long-lasting collagen, comprising the steps of:
   a) scraping extra muscle and fat tissues from a pig skin, and cutting the remaining portion of the pig skin into small tissue segments;
   b) dipping the small tissue segments into an organic solvent, and rinsing the small segment tissues until grease is removed completely;
   c) dipping the degreased small tissue segments in a salt water, and then in an acidic solution to inhibit the small segment tissues;
   d) dipping the inhibited small tissue segments to digest the small tissue segments into a second solution;
   e) perform a centrifugal separation of the second solution to separate the digested small tissue segments from the second solution;
   f) adding a salt water solution into the separated second solution to prepare a third solution, while shaking the solution severely until a cloudy substance is formed;
   g) performing a centrifugal separation to the shaken third solution to collect a lower-layer precipitate, and putting the lower-layer precipitate into water while adding sodium hydroxide to form a fourth solution;
   h) freezing the fourth solution and then drying the fourth solution to obtain a collagen;
   i) preparing the collagen into a collagen solution, and mixing the collagen solution with γ-polyglutamic acid (γ-PGA) into a fifth solution;
   j) titrating glutaraldehyde solution in the fifth solution by a pump while blending the collagen of the fifth solution and the glutaraldehyde solution to perform a first crosslinking; and
   k) titrating the glutaraldehyde solution in the fifth solution by the pump again while blending the collagen of the fifth solution and the glutaraldehyde solution to perform a second crosslinking to obtain the long-lasting collagen.

9. The manufacturing method of a long-lasting collagen as recited in claim 8, wherein in the step c), the degreased small tissue segments is dipped in the salt water with a concentration of 1% at 4° C. for 24 hours, and then in a citric acid of pH 4.5 for 24 hours to inhibit the small segment tissues.

10. The manufacturing method of a long-lasting collagen as recited in claim 9, wherein in the step d), the inhibited small tissue segments is dipped in a mixed solution of pepsin and hydrochloric acid, having a concentration of 0.5 M at 4° C. for 24 hours to digest the small tissue segments into the second solution.

11. The manufacturing method of a long-lasting collagen as recited in claim 10, wherein in the step e), the digested small tissue segments are separated from the second solution by centrifuging the second solution at 5500 g.

12. The manufacturing method of a long-lasting collagen as recited in claim 11, wherein in the step f), the salt water solution of 0.8 M is added into the separated second solution to prepare the third solution.

13. The manufacturing method of a long-lasting collagen as recited in claim 12, wherein in the step g), the shaken third solution is centrifuged at 22000 g to collect a lower-layer precipitate, and the lower-layer precipitate is put into the water while adding the sodium hydroxide with a concentration of 0.1 N to adjust the pH to 7 to form a fourth solution.

14. The manufacturing method of a long-lasting collagen as recited in claim 13, wherein in the step h), the fourth solution is frozen $-20°$ C. for 24 hours and then dried to obtain a Type I collagen.

15. The manufacturing method of a long-lasting collagen as recited in claim 14, wherein in the step i), a 35 mg/ml collagen solution is prepared from the frozen collagen and mixed 4 ml of the collagen solution with the same amount of the $\gamma$-polyglutamic acid ($\gamma$-PGA) to produce the fifth solution.

16. The manufacturing method of a long-lasting collagen as recited in claim 15, wherein in the step j), 0.5 ml of a 0.05% glutaraldehyde solution is titrated into the fifth solution by the pump for 30 minutes to perform the first crosslinking.

17. The manufacturing method of a long-lasting collagen as recited in claim 16, wherein in the step k), 0.5 ml of a 0.05% glutaraldehyde solution is titrated again into the fifth solution by the pump for 30 minutes to perform the second crosslinking.

* * * * *